(12) United States Patent
Washburn (10) Patent No.: US 10,436,865 B2
(45) Date of Patent: Oct. 8, 2019

(54) CUTTINGS ANALYSIS FOR IMPROVED DOWNHOLE NMR CHARACTERISATION

(71) Applicant: Ingrain, Inc., Houston, TX (US)

(72) Inventor: Kathryn Elizabeth Washburn, Tromso (NO)

(73) Assignee: Halliburton Energy Services, Inc., Houston, TX (US)

(*) Notice: Subject to any disclaimer, the term of this patent is extended or adjusted under 35 U.S.C. 154(b) by 98 days.

(21) Appl. No.: 15/543,576

(22) PCT Filed: Jan. 15, 2016

(86) PCT No.: PCT/US2016/013619
§ 371 (c)(1),
(2) Date: Jul. 14, 2017

(87) PCT Pub. No.: WO2016/115471
PCT Pub. Date: Jul. 21, 2016

(65) Prior Publication Data
US 2018/0003786 A1    Jan. 4, 2018

Related U.S. Application Data

(60) Provisional application No. 62/104,099, filed on Jan. 16, 2015.

(51) Int. Cl.
| | | |
|---|---|---|
| *G01V 3/00* | (2006.01) | |
| *G01R 33/48* | (2006.01) | |
| *G01R 33/44* | (2006.01) | |
| *G01V 3/32* | (2006.01) | |
| *G01N 24/08* | (2006.01) | |

(52) U.S. Cl.
CPC ....... *G01R 33/4808* (2013.01); *G01N 24/081* (2013.01); *G01R 33/44* (2013.01); *G01V 3/32* (2013.01)

(58) Field of Classification Search
CPC .................................................. G01R 33/4808
USPC .................................................. 324/303, 306
See application file for complete search history.

(56) References Cited

U.S. PATENT DOCUMENTS

| | | | |
|---|---|---|---|
| 3,135,912 A | 6/1964 | Baker et al. | |
| 8,081,802 B2 * | 12/2011 | Dvorkin | G01N 23/046 |
| | | | 175/249 |
| 9,507,047 B1 * | 11/2016 | Dvorkin | G01V 5/101 |
| 2003/0094946 A1 | 5/2003 | Galford et al. | |
| 2005/0168220 A1 | 8/2005 | Lenormand et al. | |

(Continued)

FOREIGN PATENT DOCUMENTS

EP        1548455 A1    6/2005

OTHER PUBLICATIONS

International Search Report and Written Opinion issued in corresponding International Patent Application No. PCT/US2016/013619 dated Apr. 11, 2016 (13 pages).

(Continued)

*Primary Examiner* — Louis M Arana
(74) *Attorney, Agent, or Firm* — Chamberlain Hrdlicka (57) ABSTRACT

A method for combining nuclear magnetic resonance (NMR) analysis and digital rock physics (DRP) analysis based on drilling cuttings or other rock samples for improved downhole nuclear magnetic resonance validation and characterization. A system for performing the method also is provided.

15 Claims, 2 Drawing Sheets

(56) References Cited

U.S. PATENT DOCUMENTS

| | | |
|---|---|---|
| 2006/0272812 A1 | 12/2006 | Yu et al. |
| 2010/0135536 A1 | 6/2010 | Dvorkin et al. |
| 2010/0326669 A1 | 12/2010 | Zhu et al. |
| 2012/0275658 A1* | 11/2012 | Hurley .................. G06T 7/0004 382/109 |
| 2013/0259190 A1 | 10/2013 | Walls et al. |
| 2013/0270011 A1 | 10/2013 | Akkurt et al. |
| 2016/0170088 A1* | 6/2016 | Grader .................. G01N 33/24 703/6 |

OTHER PUBLICATIONS

XP009034279, A Fast and Direct Method of Permeability Measurements on Drill Cuttings, Egermann P et al, Jan. 12002.

* cited by examiner

CUTTINGS ANALYSIS FOR IMPROVED DOWNHOLE NMR CHARACTERISATION

This application is a National Stage Application of PCT/US2016/013619, filed Jan. 15, 2016, which claims the benefit under 35 U.S.C. § 119(e) of prior U.S. Provisional Patent Application No. 62/104,099, filed Jan. 16, 2015, which is incorporated in its entirety by reference herein.

FIELD OF THE INVENTION

The present invention relates to a method for combining nuclear magnetic resonance (NMR) analysis and digital rock physics (DRP) analysis based on drilling cuttings or other rock samples for improved downhole nuclear magnetic resonance characterisation and validation. The present invention also relates to a system for the method.

BACKGROUND OF THE INVENTION

In the field of logging (e.g., wireline logging, logging while drilling (LWD), nuclear magnetic resonance (NMR) tools have been used to explore the subsurface based on the magnetic interactions with subsurface material. Some downhole NMR tools include a magnet assembly that produces a static magnetic field, and a coil assembly that generates radio frequency (RF) control signals and detects magnetic resonance phenomena in the subsurface material. Properties of the subsurface material can be estimated from the detected phenomena.

Downhole nuclear magnetic resonance can be used to provide information on pore size distributions, fluid saturations, fluid typing and permeability estimates. However, the measurements usually need to be calibrated. This is currently done in the lab environment using a well core. Well cores are very small compared to an entire formation, so multiple well cores are typically taken and analyzed and rock properties are interpolated in between geographic locations of the cores. Nevertheless, cores can be approximately a meter in length and 1/10 meter in diameter. Unfortunately, core analysis is expensive and time consuming. If the well is cored, the measurements required to calibrate the system can take weeks to months. Laboratory preparation (e.g., cleaning) and analysis of cores typically must be done off-site. Cores must be extracted and shipped to a laboratory for analysis and this can require significant time to complete. Further, physical lab experiments are difficult to perform due to the usual size and shape requirements of well samples such as cores, and the need to use sufficiently large sized samples to obtain accurate results by laboratory analysis.

Downhole NMR can be used to provide information on lithology independent porosity, pore size distributions, fluid properties, estimates of free and bound fluid and permeability. NMR functions by putting a sample in the presence of a strong magnetic field. The magnetic moments of the nuclei tend to align along the direction of the applied magnetic field ($B_0$). The nuclei then precess around at a characteristic rate defined by:

$$\omega = -\gamma B_0$$

where $\omega$ is referred to as the Larmor frequency and $\gamma$ is the gyromagnetic ratio, a fundamental constant specific to each NMR active isotope. The typical magnetic field strengths used in logging range from 0.01 T to 0.05 T such that $\omega$ is in the range of 400 kHz to 2 MHz, though other frequencies may be used.

In order to make an NMR measurement, the system must be excited away from the equilibrium. This is done by using an antenna to apply a radio frequency (rf) pulse at the Larmor frequency to tip the magnetic moments away from $B_0$. As the nuclei's magnetic moments precess around the applied magnetic field, they induced a voltage in an antenna (either the same one that excited the system or a different one specifically for detection) that is measured as the NMR signal. By different combinations of rf pulses and delays, the measurement can be made sensitive to a range of different properties such as $T_1$ relaxation, $T_2$ relaxation or diffusion.

$T_1$ relaxation is the time it takes for the magnetic moments of the nuclei to come back to equilibrium with the environment, i.e., return to alignment along the applied magnetic field. $T_2$ is the time it takes the magnetic moments of the nuclei to come to equilibrium among themselves. When the system is initially excited, all the nuclei are precessing in unison. As time progresses, the nuclei interact with each other and their environment, such that they lose synchronicity. Eventually, at long enough time, all order between the precessing magnetic moments is lost and they will be in a completely disordered state. A diffusion measurement is used to measure the diffusion coefficients of the constituents present in the sample and can be used to determine fluids present. The diffusion coefficients of the fluids may be influenced by the sample pore structure.

While NMR can measure upon nearly every element of the Periodic Table, NMR in the oil industry focusses upon the $^1$H isotope. This is because the $^1$H isotope is abundant, common in the materials of interest, and has a high NMR sensitivity. Some work has been done to look at $^{13}$C and $^{23}$Na, but this has been limited to research due to the lower isotopic abundances and weaker signals from these isotopes.

Under ideal conditions, the NMR signal is proportional to the amount of hydrogen present in the system. For conventional reservoirs that consist of sandstones and carbonates, the rock matrix itself contains very little hydrogen. Therefore, the signal is assumed to arise from the fluids saturating the pore space. By inputting the hydrogen index of the fluids, the porosity of the system can be determined. Because information on the matrix is not required, NMR is referred to as lithology independent. This makes it valuable as other types of logging tools need to know the formation lithology in order to calibrate the porosity; using limestone for porosity calculation will produce incorrect values if the lithology is really dolomite. Because lithology may change numerous times throughout the borehole, this makes accurate assessment of porosity a challenge. For shale reservoirs, the matrix may contain significant quantities of clay and organic matter, which contains hydrogen, such that determining porosity from the NMR signal may not be as straight forward. Also, for both conventional and unconventional samples, if the sample is high in paramagnetic impurities, this may lead to loss of the NMR signal and therefore the calculated porosity will be too low.

Beyond porosity measurement, NMR can provide other valuable information about the system.

One of the other common uses of NMR is to obtain a pore size distribution (PSD). Fluids have a bulk NMR relaxation rate caused by internal interactions. For brine, this is usually on the order of 2-3 s. Paramagnetic impurities in the brine may lower this time. The bulk relaxation rate of oil depends on its viscosity. The relaxation rate of methane depends on pressure. When these fluid are placed in a porous medium, they will interact with the pore surfaces. When fluid molecules encounter pore surfaces, this will cause an enhancement in the relaxation rate from the bulk rate. The enhancement is governed by the surface relaxivity parameter. The larger the surface relaxivity, the more effective the surface is in enhancing the fluid relaxation. For $T_1$, the equation relating pore size to measured $T_1$ is simple:

$$\frac{1}{T_1} = \rho_1 \frac{S}{V},$$

$\rho_1$ is the surface relaxivity for $T_1$, and S/V is the surface to volume ratio of the pore. S/V is used as a proxy for pore size; the smaller the pore, the larger its surface to volume ratio will be. As such, fluid molecules will encounter pore surfaces more frequently in small pores than in larger pores, causing the relaxation in the smaller pores to be more rapid than the larger pores. In order for the $T_1$ to be considered a reflection of the pore size distribution, $\rho_1$ must be constant throughout the pore space. The sample also needs to be in the fast diffusion regime, where fluid molecules rapidly explore the pore space but exchange between pores is slow, such that a single exponential decay value is produced for a pore of a given side. If the system is in the slow diffusion regime, the diffusion in the pore is slow compared to the relaxation. This occurs when either the surface relaxivity is very high or the pores are very large and will lead to bi- or multi-exponential decays from a single pore. If the exchange between pores is rapid, the system is said to be in the diffusional coupling regime. Here, the relaxation rates of the different pores will be averaged. This may be complete averaging, such that a single relaxation time is observed, or incomplete, where two peaks are still observed but with incorrect relaxation times and peak intensities.

The relaxation behavior for $T_2$ relaxation is more complicated than $T_1$. The observed $T_2$ relaxation time is described by:

$$\frac{1}{T_2} = \rho_2 \frac{S}{V} + \frac{D\gamma^2 G^2 Te}{12}.$$

where $\rho_2$ is the surface relaxivity for $T_2$, SN is the surface to volume ratio of the pore, D is molecular diffusion constant, γ is proton gyromagnetic ratio, G is magnetic field gradient, and Te is interecho time.

In addition to the relaxation caused by differing pore sizes, the effective $T_2$ relaxation rate can be influenced by the presence of magnetic gradients in the pore space. The magnetic gradients can arise naturally in the sample. These are referred to as internal gradients and they occur because of different magnetic susceptibility between the matrix and the saturating fluids. Because there cannot be a discontinuity in the magnetic field strength at the pore surface, magnetic gradients develop at the pore surfaces. The exact strength of the internal gradients depends on the pore shape, but the strength of the gradients can roughly be considered to be proportional to:

$$G \propto \frac{\Delta\chi B_0}{r}$$

where G is the strength of the internal gradient, Δχ is the difference in magnetic susceptibility between the pore matrix and saturating fluid and r is the pore radius. Magnetic gradients can also be applied, either through pulsed field gradients or through gradients that arise due to the design of the magnet. In order to minimise the effect of the second term, short echo spacings are used such that the effect $T_2$ time can be approximated by:

$$\frac{1}{T_2} = \rho_2 \frac{S}{V}$$

and $T_2$ can be thought to reflect the pore size distribution of the sample.

Both the $T_1$ and $T_2$ measurements give relative pore size distributions. In order for an absolute pore size distribution to be produced, the surface relaxivity needs to be determined. This is commonly done by calibration to MICP curves. However, this technique has the problem where MICP measures the pore throat size while NMR measures the pore body size. In some samples this is not an issue, but in other samples, there is frequently not a relationship. In shale samples, MICP measurements may damage the pore structure during measurement, such that the results are not an accurate reflection of the pore throat distribution. Other methods for determination of surface relaxivity relate to calibrating the relaxation times to pore size distributions measured from an imaging technique like X-ray CT or SEM. Alternatively, the surface relaxivity can be calibrated against the surface area measurements made through BET or $N_2$ adsorption. Lastly, there are common values of surface relaxivity for different rock types that can be applied if calibration is not possible.

NMR can be used to help distinguish moveable from non-moveable fluids. This can be important for low-resistivity reservoirs. In these situations, there may be significant quantities of water present in the formation, but if the water is in very small pores, capillary pressure makes it immobile and hydrocarbons can be produced from the reservoir without a large watercut. Different lithologies have different rules of thumb for $T_2$ cutoff times. Sandstones, the standard cutoff time is assumed to be 33 milliseconds (ms) while carbonates the cutoff time is 95 ms. Any signal below 3 ms is assumed to be associated with clay bound water. However, these are just rules of thumb and may vary significantly from formation to formation. Calibration is needed in order to determine the real $T_2$ cutoff time or times for the reservoir.

NMR is also used to estimate permeability. While NMR is a static measurement and therefore does not actually measure permeability, a dynamic measurement, several of the parameters it measures can be related to permeability. There are several models used to convert the NMR data to permeability. One way of estimating permeability is the SDR or Kenyon method:

$$k = C \times T_{2LM}{}^a \times \Phi^b$$

where k is permeability, C is a constant that typically 0.001, $T_{2LM}$ is NMR transverse decay time, φ is porosity, a=2 and b=4. This equation relates the pore size and porosity to permeability. The idea is that large pores and high porosity is likely to have a high permeability while samples with small pores and low porosity are likely to have lower permeability. Another method is the Timur-Coates. This relates the free and bound fluid ratios to permeability, $$k = C \times \left[\left(\frac{FFI}{BVI}\right)^a \left(\frac{\Phi}{10}\right)^b\right]$$

where k is permeability, C is typically 0.001, a=2 and b=4, φ is porosity, BVI is bulk volume irreducible fluid fraction, and FFI is free fluid fraction.

A third, less commonly used method is modifications of the Kozeny-Carman relation to relate to NMR measured properties. A frequently used equation is:

$$k = \frac{\Phi}{\tau(S/V)^2}$$

where k is permeability (e.g., in milliclarcies), φ is porosity, S/V is the surface to volume ratio of the pore, and τ is the tortuosity of the system. The tortuosity may be estimated from a variety of methods, but it often comes from diffusion measurements to relate the restricted diffusion rate to the unrestricted diffusion rate. In addition, there are other, less widely adopted methods to relate the NMR results to permeability that exist.

There may be minor differences in how these equations for calculating permeability from NMR results are written depending on the author and what the standard value of C is assumed to be. These equations can be applied uncalibrated, but the results are frequently shifted away from the true values by orders of magnitude. Because of surface relaxivity and structural differences in the rock matrix, the C term and frequently the A and B terms for a specific reservoir may differ from the standard values. The free and bound fluid estimates are frequently calculated with values estimated from using standard cutoff times, which may not be the true cutoff time for the reservoir. Both these effects make lab calibration of the equations important.

Beyond one dimensional measurements, two dimensional correlation measurements may be performed. The most common of these are the $T_2$-Diffusion and the $T_1$-$T_2$ correlation measurements. The $T_2$-diffusion is commonly used to perform fluid saturations. In the ideal situation, the diffusion axis will give information on the types of fluids present and the $T_2$ axis will tell where the fluids are located in the pore space. However, interpretation of the plots is frequently not straightforward due to the effects of internal gradients, wettability and restricted diffusion. $T_1$-$T_2$ measurements can give some indication of fluid saturations as well, but are particularly useful to identify viscosity of the constituents. Beyond these, $T_1$-Diffusion, $T_2$-Internal Gradients, $T_1$-Internal Gradients, $T_2$-$T_2$ exchange, Diffusion-Diffusion exchange, and Diffusion-Diffusion correlation measure are possible measurements, though not commonly performed downhole. While three dimensional (or more) measurements are possible, due to computation power required and the usual low signal to noise of logging measurements, they are not commonly performed.

More simple characterization of diffusion or $T_1$ may be performed using a Dual Te or a Dual Weight Time measurements.

Specialised NMR pulse sequences such as binomial editing may be used to help identify the solid content in a sample versus fluid content. It may also help distinguish kerogen from bitumen.

As indicated, in order to calibrate the NMR logs, a well core has been collected and sent to labs for measurement. Sometimes NMR measurements are made in an as-received state. This may give information regarding the core saturations. However, there are concerns of loss of signal from gas loss during core retrieval, contamination by drilling fluid and core dessication. The sample then needs to be cleaned. This step may range from a few days to a few months depending on the core permeability, type of fluids present and the type of drilling mud used. The sample is then dried and saturated with a synthetic formation brine. NMR measurements are then performed on the core in the 100% brine saturated state. Measurements may be made at ambient conditions, elevated temperature, elevated pressure or both elevated temperature and pressure. The 100% brine saturated state is the standard, but specialized tests may be done where the cores are saturated with oil or possibly a mix of fluids.

The core then needs to be desaturated. For core calibration, this is usually done with air but it may also be performed with lab oil, crude oil, or deuterated oil. Measurements made with lab oil or crude oil will likely require more advanced measurements to interpret the data, for example $T_2$-Diffusion measurements. Depending on the permeability of the system and the desaturation pressure, desaturation may take anywhere from a few days to weeks. NMR measurements are then performed on the core in the desaturated state. Measurements may be made at ambient conditions, elevated temperature, elevated pressure or both elevated temperature and pressure. The $T_2$ cutoff is then calculated by determining the $T_2$ value of the 100% saturated state that has the equivalent as the core in the desaturated state. There are concerns that the NMR results produced in the lab are not representative of downhole conditions.

In addition to the time taken for the NMR measurements, in order to calibrate the NMR permeability, lab permeability measurements must also be made. Usually these are gas permeability measurements performed between sample drying and saturation with brine, but the samples may also be calibrated to liquid permeability measurements if desired. The permeability measurement adds to the time required for the calibration. For shale reservoirs, permeability estimates on cuttings are common using the Gas Research Institute (GRI) technique. However, the accuracy of this technique is uncertain, as there are concerns regarding induced fractures.

Because coring is expensive and time consuming, lab calibration is frequently only performed on a few samples. Typical calibration project sizes range from 2-12 samples. While this is better than no calibration, the complexity of many reservoirs cannot be captured by a low number of samples. The locations of the cored samples may be suboptimal as well, as coring will have taken place before much was known about the individual well.

Some work has been done to perform NMR measurements on drilling cuttings, both at the wellsite and in the lab. There are concerns in understanding what the data from the NMR measurements on cuttings actually mean; the cuttings are assumed to be completely flushed with drilling fluid. There are also concerns of induced fractures in the cuttings from drilling. However, even if the cuttings are intact and filled with a single fluid, the only properties that can be measured with NMR are porosity and $T_1$ and $T_2$ time distributions. Rapid calibration of cutoff times and permeability cannot be performed by using NMR on cuttings.

While NMR provides valuable information about a well, it is one of the slowest logging measurements and one of the more expensive logging tools. It also has the disadvantage of low signal to noise. The low signal to noise can then make analysis of the acquired data more uncertain. Signal to noise can be improved by sacrificing logging speed or performing stationary measurements, but slowing logging speed or stop-and-go movement through an entire formation will be very time consuming.

SUMMARY OF THE PRESENT INVENTION

A feature of the present invention is a method for combining nuclear magnetic resonance (NMR) analysis and digital rock physics (DRP) analysis based on drilling cuttings or other rock samples for improved downhole nuclear magnetic resonance validation and characterisation.

A further feature of the present invention is a system for making such determinations.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method for validating subterranean rock properties of a rock formation estimated by nuclear magnetic resonance, comprising a) retrieving rock samples from each of one or more locations inside a well during drilling; b) scanning the rock samples to produce digital images of the rock samples; c) segmenting the digital images to provide segmented digital images, wherein pores, grains, and organic content are defined in the segmented digital images; d) determining at least one rock property of the rock samples using the segmented digital images; e) positioning a nuclear magnetic resonance (NMR) logging tool at the one or more locations inside a well bore of the well during the drilling or after the drilling; f) measuring in situ fluid properties and in situ rock properties in the well using the NMR logging tool at the one or more locations; g) estimating at least one rock property in the well at the one or more locations using the measured in situ well properties obtained in step f); h) comparing at least one rock property determined for the well using the NMR logging tool for at least one of the one or more locations with a corresponding at least one rock property determined for the rock samples for a corresponding at least one of the one or more locations of the well; and i) analysing and validating the at least one rock property determined using the NMR logging tool as compared to the at least one rock property determined for the rock samples for the corresponding at least one of the one or more locations of the well.

A system for performing this method is also provided.

A computer program product which can be used for implementing the method is also provided.

It is to be understood that both the foregoing general description and the following detailed description are exemplary and explanatory only and intended to provide a further explanation of the present invention, as claimed.

DETAILED DESCRIPTION OF THE PRESENT INVENTION

The present invention relates in part to a method for combining nuclear magnetic resonance (NMR) analysis and digital rock physics (DRP) analysis based on drilling cuttings or other rock samples for improving downhole nuclear magnetic resonance validation and characterisation. As indicated, NMR can yield inaccurate, anomalous or incomplete determinations for rock properties under certain well and formation conditions. To counter this potential problem, the present invention provides a workflow by which rock property estimations based on NMR data can be analysed and validated after comparison to parallel determinations of the same rock property as determined using digital rock physics (DRP) based on drilling cuttings or other rock samples obtained from the same well location. This modality of comparison and analysis can be used at one or more locations along a well bore, such as at a single location or duplicated for multiple locations along a well bore, which may extend vertically or horizontally, or other well path directions relative to the Earth's surface. The method enables NMR analysis of a well to be refined without need of core extraction for calibration.

By combining NMR logging measurements with the cuttings workflow, a significant advantage in the interpretation and value in the NMR logs can be provided. In the present invention, NMR calibration on the wells can be provided where core has not been taken. Also, well formation characterisation results on the order of a few days (within 1 day or 2 days or 3 days to 7 days) as opposed to weeks or months can be provided. There is usually a delay between drilling and NMR logging. Rapid turnaround on cuttings analysis can help guide the areas of interest for logging. By performing calibration measurements on drilling cuttings, the need for a core can be eliminated and results can be provided in shorter time periods. Immediate application of the cuttings work flow can provide rapid calibration for porosity, pore size distribution, $T_2$ cutoff times and permeability estimates, and other properties. In addition, due to rapid turnaround time between drilling and logging, suggestions can be made on regions of interest where the well operator may want to slow the NMR tool down in order to obtain better information or sped up when there is little expected information of value. Therefore, logging speed can be increased in areas of the formation that are not of interest while the tool can be slowed down, or even stopped, to gain the best quality data possible in the zones of interest.

As used herein, "drilling cuttings" refers to cuttings extracted from a drilling fluid, wherein the drilling fluid transports the drill cuttings to the Earth's surface after use of the drilling fluid in a drilling of a wellbore in a subterranean reservoir. Drill cuttings are extracted from a drilling fluid for analysis. This can be achieved by means of a shale shaker or similar device. The drill cuttings can be classified and grouped based on the time they arrive at the surface. The drill cuttings can be placed in different containers for storing and/or for the grouping of cuttings based on arrival time and extraction at the Earth's surface (e.g., for subsequent DRP analysis of one or more of separately stored groupings of cuttings). Drill cuttings may be grouped such that the downhole coordinates from which they were produced are estimated to be within about plus or minus 10 feet or more of actual, or within other proximities. As used herein, "downhole" refers to the wellbore extending into the subterranean reservoir in a direction or directions further away from its starting point, and not necessarily only vertically down, as the wellbore also can extend horizontally at least in part relative to the Earth's surface which horizontal portion(s) is (are) also considered "downhole" for purposes of the present invention. The grouped drill cuttings may be stored in a bag, canister or similar device for further processing. Optionally, the drill cuttings may then be further classified by size for example the fraction above about 60 to about 40 mesh or larger or the fraction lower than about 40 to about 60 mesh or smaller, or other fraction/cut. As an option, the fraction/cut obtained from the classification can be the fraction used for the DRP analysis. Optionally, the drill cuttings may be cleaned by washing or similar process and dried. One group of drill cuttings can be analyzed or two or more groups of drill cuttings can be analyzed and the results arranged in sequential order. The corresponding downhole coordinates of the estimated location of the drill cuttings is recorded along with the physical location of the groups of drill cuttings. Optionally, the sequential arrangement of grouped drill cuttings may be placed in one or more containers. The container may be a tube with a circular, rectangular or other cross section. The container may be an open tray. Optionally, the grouped, sequential drill cuttings may be secured by embedding them in a material to hold them securely in place. The material for this purpose may be a resin such as epoxy or similar material. The grouped, sequential drill cuttings (the target object) can be analyzed by X-ray CT scan or (FIB-) SEM. Individual rock properties can be determined based on the segmented digital images obtained on the drilling cuttings, which correspond to rock properties determined or to be determined based on NMR logging in the same well bore from which the drill cuttings are acquired at similar locations or intervals. Then, scans, such as single or dual-energy X-ray CT or (FIB-)SEM scans can be done on groups of cuttings extracted at intervals in the well bore (such as at 10 foot (approx. 3 meter) regular intervals or about 50 feet (15 meter) to 500 feet (150 meter) regular intervals, or other regular intervals or distances, irregular intervals, or at selected vertical or lateral or other directional depth locations within the well bore), which correspond to locations where NMR scanning is/will be planned to be performed or has been performed. Well path locations along the well bore may be estimated and/or described by coordinates, such as by using spatial coordinate systems used in the industry.

The NMR measurements can be performed by downhole NMR tools. The NMR measurement processes can be performed by a downhole NMR tool while the tool is disposed within a wellbore during well system operations. The downhole NMR tool can be suspended in the wellbore for wireline logging, or the downhole NMR tool can be coupled to a drill string for NMR logging while drilling (LWD). The logging tool may be a triple combination tool ("Triple Combo") or Modular Formation Dynamics Testing Tool (MDT), that combines an NMR tool with at least one different tool, such as a density tool.

While NMR measurements are supposed to be lithology independent, even if the rock matrix (non-void, non-fluid material of sample) contains no hydrogen, knowledge of the hydrogen index of the drilling fluid or fluids usually is required to produce an accurate porosity. If these values are incorrect, the porosity will be systematically too high or too low. If there are changes in formation salinity or hydrocarbon properties, this may also introduce errors in the porosity calibration. By calculation of porosity (e.g., total or effective porosity) from X-ray computer tomographic (CT) or scanning electron microscopy (SEM) or focused ion beam-SEM images, a check can be provided that the NMR values are correct. If there are high quantities of paramagnetics in the formation, this can lead to signal loss in the NMR signal and in turn the porosity calculated from it. This may be more of a possibility for a vertically-oriented well bore than for a horizontally-oriented well bore. Laser induced breakdown spectroscopy (LIBS) and X-ray fluorescence (XRF) measurements can be used to check for the possible presence of paramagnetic impurities that may be leading to NMR signal loss.

For shales, the NMR signal may contain contribution from non-porosity hydrogen, e.g., clays or organic matter. Comparison of porosity values from X-ray CT or SEM (SEM or FIB-SEM), information on organic matter, either from SEM images, Fourier transform infrared spectroscopy (FTIR) or LIBS and mineralogy from XRF, energy dispersive spectral analysis (EDS), FTIR, X-Ray diffraction (XRD) or LIBS can be used to correct the NMR signal for the influence of hydrogen not arising from fluid filled porosity. The determined clay content can be used to estimate the amount of clay-bound water and help select the clay-bound water cutoff time in the logs.

NMR measurements on a single phase, low viscosity fluid can be assumed to relate to the pore size distribution in the sample. In this situation, a straightforward calibration of the surface relaxivity value or values for the logs can be provided. However, the NMR signal may deviate from this ideal situation due to diffusional coupling, the slow diffusion regime or internal gradients. An improved correction can be created for diffusion coupling in the logs based on the NMR response and the imaged pore size distributions. The present invention can calculate, from the images, the internal gradients present in the pore space and can provide a correction value or function. In the case of partial saturation, the present invention can determine the surface relaxivity for the different phases present. This may require calculation of capillary pressure to determine which portions of the pore space are saturated by what fluid. Because relationships between paramagnetic content of iron (Fe) and manganese (Mn) and surface relaxivity are known, the surface relaxivity can also be calculated from XRF or LIBS measurements.

In order to better interpret the NMR results, the present invention can create forward models from the imaged pore size distribution to determine the fluid types and locations that would best produce the resulting relaxation results. These may use NMR fluid behaviour calculated from standard equations or can input information on NMR measurements on actual fluids. Given the low signal to noise ratio of the NMR logging tool, the simulated NMR responses can help confirm whether the resulting relaxation distributions are reasonable as well as provide confidence in the produced results. Monte Carlo tests, where the results are tested numerous times with different random noise added can provide information on the stability and accuracy of the NMR inversions.

Capillary pressure simulations can be used to provide the free and bound fluid estimates plus the $T_2$ cutoff times. The present invention can rapidly determine how much of the fluid is mobile and immobile for a given capillary pressure. These numbers could be directly applied to the logs or fed into simulations of the $T_2$ response from imaged pore size distributions.

For NMR permeability, instead of performing laboratory measurements on core, which is time consuming, the present invention can calculate the permeability of the cuttings from the SEM (SEM or FIB-SEM) images or from 3D x-ray CT measurements. This could be done from either the 3D images or from the 2D permeability calculations. The simulated permeability can then be related to the NMR results in several ways. Firstly, the present invention can just calibrate the standard NMR permeability equations to the simulated permeability values. This could be done on actual log data or simulated NMR data. In addition to the simulated measurements, the present invention can apply the permeability trend calculations to create permeability values for the NMR log data.

Beyond the traditional NMR permeability calculations (Kenyon, Timur-Coates, Kozeny-Carman), independent trends may be observed between the NMR signal and the digital rock physics (DRP) permeability. These trends may be done manually (e.g., by eye) or through cluster analysis, machine learning, multivariate analysis (e.g., pca, pls, per) or metaheuristics. Current NMR permeability models focus only on single phase permeability, but the present invention can expand to relative permeability trends such that the NMR log can be used to estimate the relative permeability along the length of the well.

In addition, inversion of two dimensional and three dimensional NMR data is challenging as the problems are ill-posed. Forward models from the pore space could be created in order to help interpret the NMR results. These could use simulated or data measured on the actual fluids or rocks. In addition, the present invention can provide constraints to directly improve the inversion itself. Constraints may come from image analysis of the pore and matrix structure from SEM, FIB-SEM (focused ion beam combined with SEM) or X-ray data, fluid behavior from permeability and capillary pressure simulations or information on mineralogical or elemental content from XRD, SEM, SEM-EDS, FIB-SEM, XRF, FTIR, or LIBS. For example, the pore size distributions can be known or determined and then one can calculate the effect of restricted diffusion on fluids based on pore size. These will limit the possible solution space, making inversion of two dimensional and three dimensional data sets easier and faster to analyse, process or interpret.

In conventional samples, surface relaxivity stems from paramagnetic impurities in the samples. In shale samples, a different sort of surface relaxivity may arise. The organic pores may have a surface relaxivity that stems from dipolar coupling between the organic pore surfaces and fluid molecules. The dipolar coupling strength is described by:

$$D_{ij} = -\frac{\mu_0 \gamma^2 \hbar}{4\pi r_{ij}^3}\left(\frac{3\cos^2\theta_{ij}-1}{2}\right)$$

where $\mu_0$ is the permittivity of free space, $\gamma$ is the gyromagnetic ratio, hbar is Planck's constant, r is the distance between the two coupled atoms and $\theta$ is the angle the two coupled atoms make with the applied magnetic field. Therefore, the strength of the coupling depends not only on the distance between the coupled atoms, but the angle they make with the applied magnetic field. This means that the surface relaxivity of a pore will not only be dependent on its shape, but the angle the pore makes with the applied magnetic field. The effect of the dipolar coupling on relaxation rate can be described by $$T_{2H} = \frac{1}{D}.$$

As such, the surface relaxivity of a pore will $$\rho_D = \left(\frac{n_H}{T_{2H}+\tau_H}\right),$$

where $n_H$ is the number of hydrogen atoms in the pore. This relates to the H/C and H/O ratio and can be calibrated through programmed pyrolysis or LIBS. $\tau_H$ relates to the surface residency time of the fluids and this depends on the activation energy and the system temperature.

Unlike in conventional samples, surface relaxivity can no longer be assumed to be constant throughout the pore space. The present invention can estimate and optionally correct for the spread of surface relaxivity present. Another concern is the possibility of anisotropy in the NMR signal. The present invention can calculate the likelihood of this occurring and use it to aid interpretation of the logging results.

Currently, NMR has been used in conjunction with density measurements obtained using a logging tool as a way to estimate kerogen or organic matter content. The technique is similar to the Density-NMR used to estimate gas in a reservoir. A NMR logging tool and a density tool may be used in separate logging passes or separately on the same drilling string in a single logging pass (e.g., by using a triple combination tool string), to measure density and/or porosity, and optionally additional properties. Because the density of organic matter can be similar to that of water (i.e., 1 g/cc), organic matter is seen as (fluid-filled) porosity by the density tool. In contrast, because the relaxation time of organic matter is typically too short to be measured by logging tools, it is seen as rock matrix by the NMR tool. The present invention can provide verification of the results or as calibration; while the NMR-Density log may provide the trends of organic matter, it may be systemically too high or low or there may be other effects at play such that there is not a consistent trend in the error in organic matter calculation. The present invention can provide geochemical information through programmed pyrolysis, SEM (e.g., SEM or FIB-SEM) images, apparent transformation ratio, FTIR or LIBS to provide organic matter (TOC) content.

While cuttings will likely produce the most rapid results, these measurements may also be performed on whole core, core plugs or sidewall cores. In addition to NMR well log results, the methods can be used to improve lab measurements or incorporate information from lab NMR calibration measurements to constrain results.

An alternative method of NMR log calibration is provided and can potentially provide more understanding to the results than traditional calibration methods.

Calibration of NMR results are typically done by a core analysis lab. With the present invention, a more rapid way to calibrate the NMR results is provided and this provides extra value to the well operator that does not require core.

Figure 1:
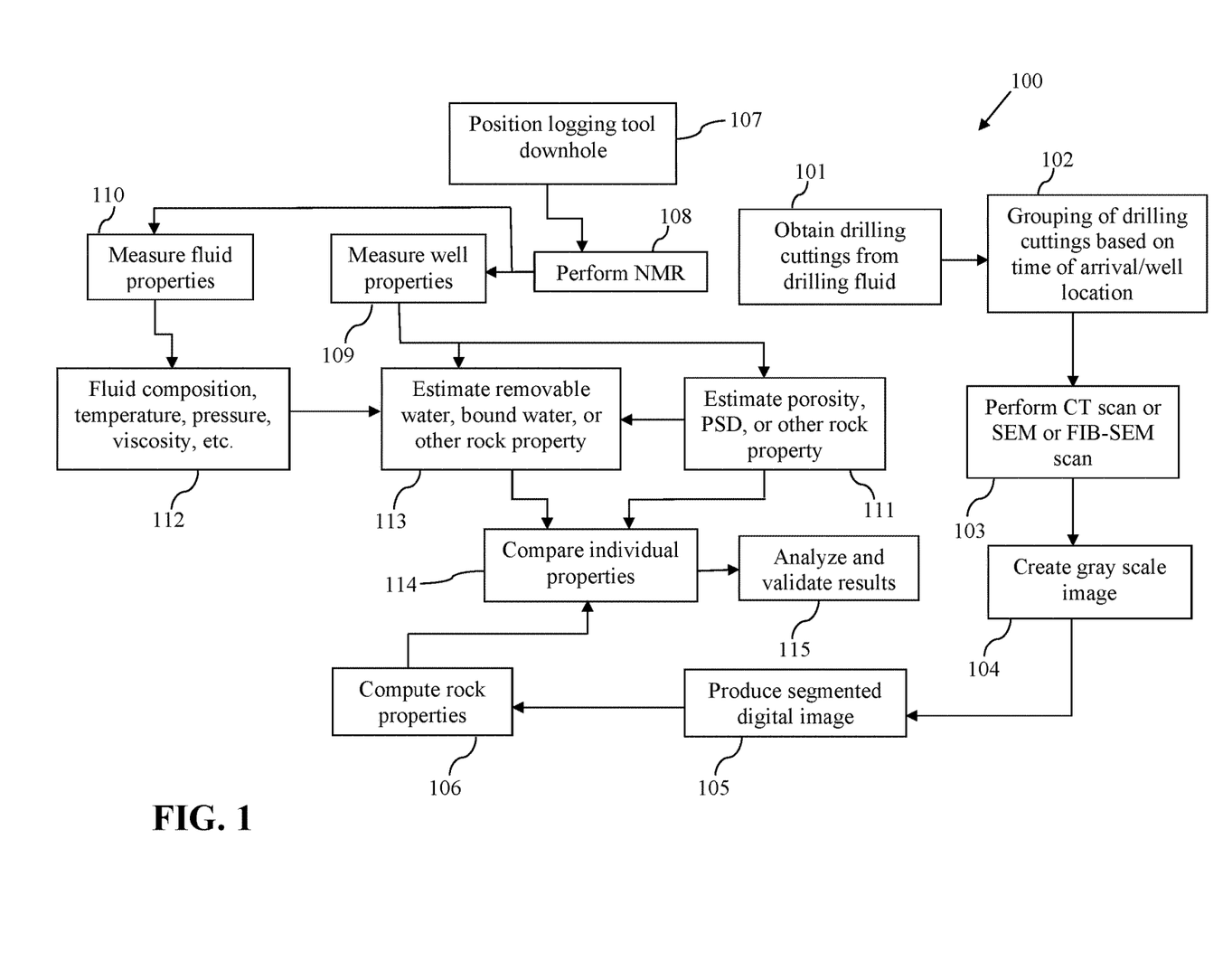
FIG. 1 is a flow chart of a method for integrating NMR logging tool analysis and digital rock physics analysis to analyse and validate rock properties determined by NMR according to an example of the present invention.

Referring to FIG. 1, a process is shown for characterising and validating subterranean rock properties of a rock formation estimated by nuclear magnetic resonance, which includes steps shown therein. In process (100) illustrated in this figure, for example, steps (101), (102), (103), (104), (105). (106), (107), (108), (109), (110), (111), (112), (113), (114), and (115) are included, wherein steps 101-106 relate to a workflow to determine one or more rock properties using DRP based on drilling cuttings obtained from the well, and steps 107-113 relate to a workflow to determine one or more rock properties based on NMR data obtained from the well bore at similar locations as from which the drilling cuttings were obtained, and steps (114) and (115) relate to combination of the results from the DRP and NMR analyses for comparison, analysis, and validation of the NMR determinations. Some of the steps are included which are described in further detail elsewhere herein, and reference can be made thereto. Other steps in FIG. 1 are further described below.

Referring to step 103, a CT, SEM, or FIB-SEM scan of the drilling cuttings (e.g., grouping of drilling cuttings) retrieved from the well location or interval of interest can be performed. For coarser samples such as carbonates or sandstones, a lower resolution CT scanner may provide sufficient resolution. When smaller pore samples are involved, such as some shales are tested, a higher resolution CT scanner may be useful. In addition, very dense rock formations, such as some shales, can require resolution beyond X-ray CT scanners. In this case, scanning electron microscopes can be used instead, such as a SEM or FIB-SEM. In general, the SEM instrument used is selected based on how small the pores in the rock are and how much resolution is needed to produce a usable image. As an option, a series of 2D images of the sample can be obtained with a FIB-SEM scanner which can be integrated into a 3D image volume by processing of the images at the scanner or an external computer. As indicated, the choice of scanner can depend upon the size of the grains and pores in the rock sample. It is common that one scanner is used, but more than one scanner may be used if a low resolution scan is initially used to scout and select an appropriate area on the rock for a higher resolution scan. The voxel size of the images obtained with the CT or SEM scanner can depend on the type of scanner used and the resolution. For X-ray CT scanners (typically used for carbonates and sandstones), the voxel size can range, for example, from about 500μ (microns) to about 65μ, or other resolutions For scanning electron microscopes (SEM) (typically used for shales), the voxel size can range, for example, from about 20 nm (nanometers) to about 5 nm, or other resolutions. The scanners typically output a series to two-dimensional arrays of values representing the gray scale values from the scanner. For X-ray CT scans, a plurality, e.g., approximately 1000 scans or other values, for example, can be used to produce the "stack" of "images". There is no technical reason why this number could not be changed. For SEM scans, the resolution can be set at 5 nm, 7.5 nm, or 10 nm, or other values, and the number of scans can be adjusted depending on the thickness of the samples.

For step 104, gray scale image creation of this step is produced from the arrays generated by the CT scanner, SEM, or FIB-SEM in the previous step 103. Software supplied with the scanning machine tomographically may reconstruct a digital 3D volume in an ordered array of voxels.

In step 105, as an option, the segmentation process can classify individual pixels/voxels as either grain, pore, or organic matter. A two- or three-dimensional digital representation can be created of the CT or (FIB-)SEM scanned cuttings, for example, which comprises one or multiple, ordered planes of voxels wherein each of the voxels can represent a pore or type of solid material (e.g., grain or organic content). As indicated, preferably more than one type of solid material is identified in the porous medium of the sample, including at least organic matter, and other kinds of solid materials such as mineral and pyrite (or high density material in general). The segmentation process is necessary due to the resolution of the scanner as compared to the size of the grains and pores in the porous medium. A number of methods to segment the 2D or 3D gray scale representation, as applicable, can be used for this purpose. As an example, the sets of image data can be analyzed to allocate or segment pixels in the two-dimensional gray scale images to different phases (e.g., pore space, organic material, mineral or pyrite in some rock samples) to form base analyzed twoLdimensional images. The value ascribed to each pixel of the 2D slices is typically an integer that may vary, for example, between zero and 255, for example, where 0 is, e.g., pure black, and 255 is pure white. Such an integer is typically referred to as a "gray scale" value. In the example given, 0 to 255 can be associated, for example, with eight digital bits in a digital word representing the gray scale value in each pixel. Other gray scale ranges may be associated with longer or shorter digital words in other implementations, and the range of 0 to 255 is not intended to limit the scope of the invention. As an option, for the purpose of simulating a process using such a numerical object (the gray scale) for a rock sample, allocating of the pixels can comprise allocating the pixels in the images to pore space, organic matter, mineral or pyrite by determining if the pixel meets preselected threshold criteria based on gray scale values preselected for these classes of material, respectively. The numerical object can be processed, for example, so that all of the pixels allocated to the void space in a rock sample (pore space) are represented by a common numerical value, e.g., by only zeros, and all of the pixels associated with the organic material, rock mineral, or pyrite are represented by different (e.g., progressively higher) numerical values, for example, a value or range value closer to 255 for pyrite (brightest), an intermediate values or range values between that of pyrite and pore for mineral (next brightest) and organic matter. One such method, for example, is described by Nur in U.S. Pat. No. 6,516,080, which is incorporated herein by reference in its entirety. Other gray scale and segmentation processes which can be adapted for use in the present methods are shown in U.S. Patent Application Publication Nos. 2010/0128932 A1, 2013/0094716 A1, 2013/0259190 A1, which are incorporated herein by reference in their entireties. Any method capable of producing a digital 2D or 3D representation of a porous medium can be sufficient for the present invention. These and other segmentation methods and techniques may be applied or adapted for use in a method and system of the present invention.

Referring to step 106, as an example, in an option total porosity ϕ can be estimated as the number of pore space pixels divided by the total number of pixels in 2D segmented digital images obtained from the scanning, gray-scaling and segmenting steps 103-105. Porosity may be determined by other methods based on DRP using 2D or 3D segmented digital images. Other rock properties, such as effective porosity, removable (free) water volume, bound water volume, pore size distribution (PSD), connected porosity, absolute permeability, relative permeability, capillary pressure, m and n Archies constants, elastic moduli, and/or electrical properties, or other properties, can be determined using known or adapted known methods applied in DRP.

Referring to step 107, an NMR tool can be lowered via a wireline (not shown) from a surface rig (not shown) into a well borehole (not shown) penetrating an earth formation (not shown), such as using known equipment configurations for this purpose, wherein the well borehole is drilled before the NMR tool and any other formation evaluation tool is/are lowered into the borehole. The NMR tool can be used as the sole formation testing tool on a wireline in the well bore or form part of a tool string (not shown) that can be conveyed into and out of a borehole with the same wireline.

For step 108, NMR measurements can be made with a formation tester having that capability. NMR measurements are made by the NMR tool at desired locations or intervals as it passes through the well bore. The NMR tool can be continuously conveyed through the well bore, which may be a constant speed, or a varied speed wherein locations/interval of greater interest may be passed at slower speed or the unit temporarily stopped at the location for NMR scanning before renewing the conveying of the unit through the wellbore. As an option, NMR measurements can be provided by a Combinable Magnetic Resonance tool known by the acronym CMR (or equivalents thereof). An example of methods of performing a CMR test which may be adapted to the present methods include those shown in U.S. Patent Application Publication Nos. 2008/136410 A1 and 2011/0054796 A1, which are incorporated herein by reference in their entireties. Typically, a borehole contains a combination of fluids such as water, mud filtrate, formation fluids, etc., which is not shown in the figures to simplify the illustrations.

Referring to steps 109-113, the in situ well properties that can be determined in step 109 from the NMR scanning can comprise T1 and T2 relaxation times, hydrogen index, temperature, pressure, resistivity, gamma, neutron-density, downhole images, well bore gauge, or any combinations thereof, or other properties. The fluid properties that can be determined in steps 110 and 112 from NMR scanning can comprise temperature, pressure, viscosity, hydrogen index, chemical composition, or any combinations thereof, or other properties. The rock properties that can be determined in steps 111 and/or 113 using the well properties alone (step 111), or in combination with the fluid properties (step 113), can be the same as those indicated for the DRP analysis. Porosity, for example, can be estimated from the NMR (CMR) test results of steps 108 and 109 in any conventional manner applied for that purpose.

Referring to step 114, the estimated rock properties derived from in situ NMR logging measurements and computed individual rock properties from digital rock physics can be compared in several ways. As an option, they can simply be compared, value to value. As another option, values from the different kinds of measurements (NMR and DRP) of the same or different rock locations can be plotted for comparison and/or curve analysis.

Referring to step 115, the analysis part of this step is different from the comparing step 114 in that mismatches in values can be evaluated so that conclusions or implications are drawn from the comparisons. Where NMR- and DRP-derived rock properties are compared value to value, for example, a preselected tolerance may be applied to the compared values in step 114. In an option, if any absolute numerical difference in the NMR- and DRP-derived rock property values falls within a preselected tolerance (e.g., ±1% or other selected values, which may vary depending on the parameter and other considerations), then the NMR-derived rock property can be considered as "validated." On the other hand, as an option, if any absolute numerical difference in the NMR- and DRP-derived rock property values falls outside a preselected tolerance, then the NMR-derived rock property can be further analysed to try to obtain an understanding of the source of the discrepancy in the NMR- and DRP-derived rock property values. As an option, if a mismatch in values occurs between the NMR- and DRP-derived rock property values that exceeds a preselected tolerance or other criteria, then a validation checklist can be applied by computer programming or manually by the operator to investigate the source of the mismatch. As an example, if NMR-determined total porosity was 10%, and DRP-determined total porosity was 8%, and a preselected 1% tolerance was being applied to this parameter for the analysis, then the 2% difference of the NMR- and DRP-derived values would necessitate further analysis. As an option, a checklist can be applied that requires taking into account effects of pre-identified possible factors on the NMR results such as 1) fluid content, 2) fluid temperature, 3) diffusional coupling, 4) H index, 5) paramagnetic content, and/or other factors. As an example, small pores sizes in the samples may be correlated with diffusional coupling effects. If source of the mismatch can be predicted or determined in this manner, then decision can be made on whether to adjust the NMR-value, such as by substituting the DRP-derived value or adjusting the NMR-derived value according to a corrective function, or eliminating use of the NMR-derived value for the rock property for the given well location or interval. This workflow provides quality control for use of NMR scanning in determining rock properties in a formation being drilled.

Figure 2:
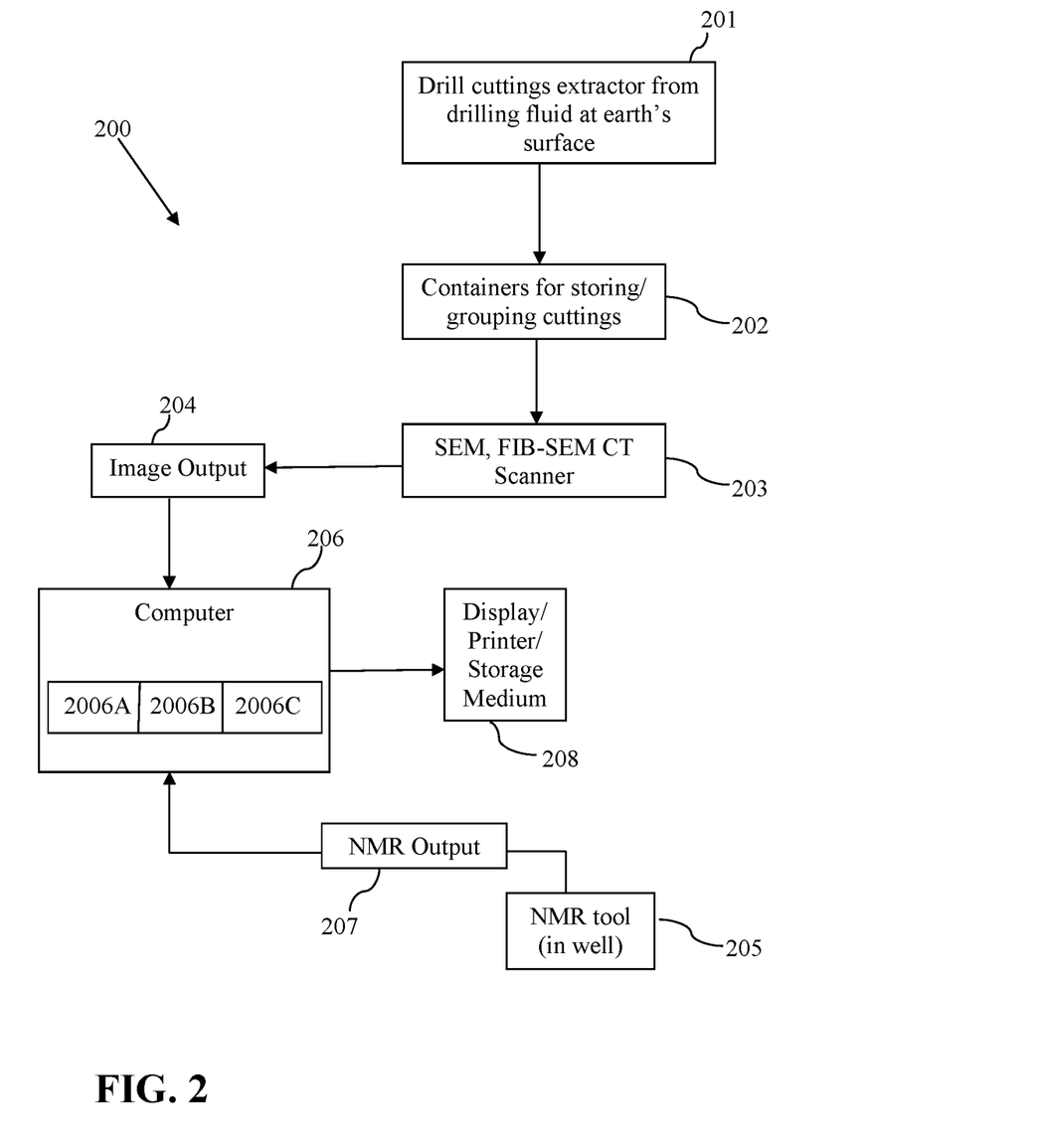
FIG. 2 shows a system which is useful for performing the process of FIG. 1 according to an example of the present application.

Referring to FIG. 2, a system (200) is shown which can be adapted for performing the present methods. As shown in this example, a drill cuttings extractor (201), such as a shale shaker, is used to extract drill cuttings from a drilling fluid. As indicated, these extracted drill cuttings can be grouped based on time of arrival at the surface. The different groupings of cuttings can be stored in separate containers (202). A classifier (not shown) optionally can be used to classify the drill cuttings by size, specific depth interval, or other parameter. The classifier, if used, can be a stack of mesh sieve trays. Two dimensional (2D) or three dimensional (3D) digital images of the drill cuttings can be generated by a SEM, FIB-SEM or X-ray CT scanner (203). The CT scanner can comprise, for example, a single energy or dual-energy X-ray multi-energy computer tomographic (CT) scanner, or similar device capable of producing a two or three dimensional digital image of the drill cuttings. As an option, a series of 2D images of the sample can obtained with a FIB-SEM scanner which can be integrated into a 3D image volume by processing of the images at the scanner or an external computer. The digital image output (204) of the scanner can be transferred to at least one computer (206) having program instructions for carrying out the digital image analysis for rock parameter determinations based on DRP. A NMR tool 205 is used to scan the wellbore to generate NMR data output 207, which is transmitted to the computer 206 having program instructions for carrying out the NMR data analysis for rock parameter determinations based on the NMR scanning results. The respective rock parameters determined from the digital image analysis and NMR analysis are compared, and then can be analysed and validated according to program instructions for carrying these steps, to generate output/results which can transmitted to one or more devices (208), such as a display, a printer, non-transitory data storage medium, or combinations of these. The computer programs used for digital image analysis and any simulation modeling can be stored, as a program product, on at least one computer usable storage medium (2006B) (e.g., a hard disk, a flash memory device, thumb drive, a compact disc, a magnetic tape/disk, or other media, including non-transitory storage media) associated with at least one processor (2006A) (e.g., a CPU or GPU) which is adapted to run the programs, or may be stored on an external computer usable storage medium (not shown) which is accessible to the computer processor. Different processors may be used for different operations performed in the methods of the present invention. Computer (206) can include at least one non-transitory readable memory unit (2006C) for storage of the programs, input data and output data, and other program results, and/or combinations of these. For output display, device (208) can be, for example, a display monitor, CRT, or other visual means of display (not shown). The computer (206) may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of system (200) including cuttings extractor (201), containers (202), scanner (203), NMR tool (205), computer (206) and indicated components thereof, and output display, printer and/or external data storage (208), can be connected to each other for communications (e.g., data transfer, etc.), via any of hardwire, radio frequency communications, telecommunications, internet connection, or other communication means. It is to be understood that the methods described herein may be implemented in various forms of hardware, software, firmware, special purpose processors, or any combination thereof.

The present invention includes the following aspects/embodiments/features in any order and/or in any combination:

1. The present invention relates to a method for validating subterranean rock properties of a rock formation estimated by nuclear magnetic resonance, comprising
    a) retrieving rock samples from each of one or more locations (e.g., a single location or multiple locations) inside a well during drilling;
    b) scanning the rock samples to produce digital images of the rock samples;
    c) segmenting the digital images to provide segmented digital images, wherein pores, grains, and organic content are defined in the segmented digital images;
    d) determining at least one rock property of the rock samples using the segmented digital images;
    e) positioning a nuclear magnetic resonance (NMR) logging tool at the one or more locations inside a well bore of the well during the drilling or after the drilling;
    f) measuring in situ fluid properties and in situ well properties in the well using the NMR logging tool at the one or more locations;
    g) estimating at least one rock property in the well at the one or more locations using the measured in situ well properties obtained in step f);
    h) comparing at least one rock property determined for the well using the NMR logging tool for at least one of the one or more locations with a corresponding at least one rock property determined for the rock samples for a corresponding at least one of the one or more locations of the well; and
    i) analysing and validating the at least one rock property determined using the NMR logging tool as compared to the at least one rock property determined for the rock samples for the corresponding at least one of the one or more locations of the well.
2. The method of any preceding or following embodiment/feature/aspect, wherein step a) comprising:
    i) extracting drill cuttings from a used drilling fluid at the Earth's surface, wherein the drilling fluid transports the drill cuttings to the Earth's surface after use of the drilling fluid in a drilling of a wellbore in a subterranean reservoir;
    ii) grouping the drill cuttings into a group of cuttings based on a time of arrival of the drill cuttings at the Earth's surface;
    iii) repeating steps i) and ii) at least once to provide a plurality of groups of drill cuttings that arrive sequentially at different recorded times at the Earth's surface which are correlated with a location within the well.
3. The method of any preceding or following embodiment/feature/aspect, wherein ii) comprises estimating downhole coordinates from which the group of cuttings were produced to within about plus or minus 10 feet of actual downhole location.
4. The method of any preceding or following embodiment/feature/aspect, wherein the extracting of the drill cuttings from the drilling fluid in i) comprises separating the cuttings from the drilling fluid with a shale shaker.
5. The method of any preceding or following embodiment/feature/aspect, wherein two or more groups of drill cuttings are analyzed in d), e), f) and g), wherein corresponding downhole coordinates of estimated locations of each of two or more groups of drill cuttings is recorded along with the physical location of the groups of drill cuttings.
6. The method of any preceding or following embodiment/feature/aspect, wherein the scanning in step b) of the rock samples is done using X-ray computer tomographic scanning or scanning electron spectroscopy to produce the digital images of the rock samples.
7. The method of any preceding or following embodiment/feature/aspect, wherein the well bore is vertically-oriented relative to Earth's surface and further comprising measuring paramagnetic content of the rock samples using laser induced breakdown spectroscopy (LIBS) or X-ray fluorescence (XRF) measurements.
8. The method of any preceding or following embodiment/feature/aspect, wherein the well bore is horizontally-oriented relative to Earth's surface.
9. The method of any preceding or following embodiment/feature/aspect, wherein the NMR logging tool is passed through the well bore using a logging wire or measurement/logging while drilling (M/LWD).
10. The method of any preceding or following embodiment/feature/aspect, wherein the NMR logging tool is used in combination with a density logging tool.
11. The method of any preceding or following embodiment/feature/aspect, wherein the fluid properties comprise temperature, pressure, viscosity, hydrogen index, chemical composition, or any combinations thereof.
12. The method of any preceding or following embodiment/feature/aspect, wherein the in situ well properties comprise T1 and T2 relaxation times from NMR, diffusion measurements, T1-T2 correlations, T2-diffusion correlations, T1-diffusion correlation, hydrogen index, temperature, pressure, resistivity, gamma, neutron-density, downhole images, well bore gauge, or any combinations thereof.
13. The method of any preceding or following embodiment/feature/aspect, wherein the rock properties comprise total porosity, effective porosity, removable (free) water volume, bound water volume, pore size distribution, connected porosity, absolute permeability, relative permeability, capillary pressure, m and n Archies constants, elastic moduli, electrical properties, or any combinations thereof.
14. The present invention also relates to a system for validating subterranean rock properties of a rock formation estimated by nuclear magnetic resonance, comprising
    (a) a drill cutting collection unit for extracting drill cuttings from a drilling fluid in groups of drill cuttings based on a time of arrival of the drill cuttings at the Earth's surface and placing the groups of drill cuttings in respective containers;
    (b) a SEM, FIB-SEM, or X-ray CT scanner having a stage capable of holding at least one of the groups of drill cuttings, and optionally including the container that holds the group of drill cuttings, operable to produce digital images of at least one or more of the drill cuttings, and operable to output the digital images to at least one computer;

(c) a NMR logging tool positionable inside a well borehole and operable for measuring in situ fluid and well properties in at least one well interval in a well, and operable to output acquired data to the at least one computer;

(d) the at least one computer comprising at least one computer processor programmable for (i) segmenting the digital images of the drill cuttings to define pores, grains and organic content in the digital image, (ii) determining at least one rock property of the rock samples using the segmented digital images; (iii) estimating at least one rock property in the well at one or more locations using measured in situ well properties obtained using the NMR logging tool; (iv) comparing at least one rock property determined for the well using the NMR logging tool for at least one of the one or more locations with a corresponding at least one rock property determined for the rock samples for a corresponding at least one of the one or more locations of the well; and (v) analysing and validating the at least one rock property determined using the NMR logging tool as compared to the at least one rock property determined for the rock samples for the corresponding at least one of the one or more locations of the well, and vi) outputting the results to at least one device to display, print, or store results of the computations; and (e) at least one device to display, print, or store results of one or more computations of step (d).

15. A computer program product on a computer readable medium that, when performed on a processor in a computerized device provides a method for performing computations of at least one or more or all of steps of any preceding claim, such as steps c), d), f), g), h), and/or i) of preceding claim 1.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for validating subterranean rock properties of a rock formation estimated by nuclear magnetic resonance, comprising a) retrieving rock samples from drill cuttings within a used drilling fluid from a defined location inside a well during drilling;
b) scanning the rock samples to produce digital images of the rock samples;
c) segmenting the digital images to provide segmented digital images, wherein pores, grains, and organic content are defined in the segmented digital images;
d) determining rock property for at least one of the rock samples using the segmented digital images;
e) performing nuclear magnetic resonance (NMR) logging of the well with an NMR logging tool during the drilling or after the drilling;
f) measuring in situ fluid properties and in situ well properties in the well using the NMR logging tool;
g) estimating a rock property in the well at the defined location using the measured in situ well properties obtained in step f);
h) comparing the estimated rock property for the defined location with the determined rock property for the defined location; and
i) analysing and validating the estimated rock property for the defined location inside the well.

2. The method of claim 1, wherein step a) comprises:
i) extracting additional drill cuttings from the used drilling fluid at the Earth's surface, wherein the drilling fluid transports the drill cuttings to the Earth's surface after use of the drilling fluid in the drilling;
ii) grouping the drill cuttings into a group of cuttings based on a time of arrival of the drill cuttings at the Earth's surface;
iii) repeating steps i) and ii) at least once to provide a plurality of groups of drill cuttings that arrive sequentially at different recorded times at the Earth's surface which are correlated with a location within the well.

3. The method of claim 2, wherein ii) comprises estimating downhole coordinates from which the group of cuttings were produced to within about plus or minus 10 feet of actual downhole location.

4. The method of claim 2, wherein the extracting of the drill cuttings from the drilling fluid in i) comprises separating the cuttings from the drilling fluid with a shale shaker.

5. The method of claim 1, wherein two or more groups of drill cuttings are analyzed in d), e), f) and g), wherein corresponding downhole coordinates of estimated locations of each of two or more groups of drill cuttings is recorded along with the physical location of the groups of drill cuttings.

6. The method of claim 1, wherein the scanning in step b) of the rock samples is done using X-ray computer tomographic scanning or scanning electron spectroscopy to produce the digital images of the rock samples.

7. The method of claim 1, wherein the well bore is vertically-oriented relative to Earth's surface and further comprising measuring paramagnetic content of the rock samples using laser induced breakdown spectroscopy (LIBS) or X-ray fluorescence (XRF) measurements.

8. The method of claim 1, wherein the well bore is horizontally-oriented relative to Earth's surface.

9. The method of claim 1, wherein the NMR logging tool is passed through the well bore using a logging wire or measurement/logging while drilling (M/LWD).

10. The method of claim 1, wherein the NMR logging tool is used in combination with a density logging tool.

11. The method of claim 1 wherein the fluid properties comprise temperature, pressure, viscosity, hydrogen index, chemical composition, or any combinations thereof.

12. The method of claim 1, wherein the in situ well properties comprise T1 and T2 relaxation times from NMR, diffusion measurements, T1-T2 correlations, T2-diffusion correlations, T1-diffusion correlation, hydrogen index, temperature, pressure, resistivity, gamma, neutron-density, downhole images, well bore gauge, or any combinations thereof.

13. The method of claim 1, wherein the rock properties comprise total porosity, effective porosity, removable (free) water volume, bound water volume, pore size distribution, connected porosity, absolute permeability, relative permeability, capillary pressure, m and n Archies constants, elastic moduli, electrical properties, or any combinations thereof.

14. A system for validating subterranean rock properties of a rock formation estimated by nuclear magnetic resonance, comprising
  (a) a drill cutting collection unit for extracting drill cuttings from a drilling fluid in groups of drill cuttings based on a time of arrival of the drill cuttings at the Earth's surface and placing the groups of drill cuttings in respective containers;
  (b) a SEM, FIB-SEM, or X-ray CT scanner having a stage capable of holding at least one of the groups of drill cuttings, operable to produce digital images of at least one or more of the drill cuttings, and operable to output the digital images to at least one computer;
  (c) a NMR logging tool positionable inside a well borehole and operable for measuring in situ fluid and well properties in at least one well interval in a well, and operable to output acquired data to the at least one computer;
  (d) the at least one computer comprising at least one computer processor programmable for (i) segmenting the digital images of the drill cuttings to define pores, grains and organic content in the digital image, (ii) determining at least one rock property of the rock samples using the segmented digital images; (iii) estimating at least one rock property in the well at one or more locations using measured in situ well properties obtained using the NMR logging tool; (iv) comparing the determined rock property with the estimated rock properly for a corresponding at least one of the one or more locations of the well; and (v) analysing and validating the estimated rock property for the corresponding at least one of the one or more locations of the well, and vi) outputting the results to at least one device to display, print, or store results of the computations; and
  (e) at least one device to display, print, or store results of one or more computations of step (d).

15. A non-transitory computer readable medium comprising instructions that, when performed by a processor perform a method for:
  c) segmenting the digital images to provide segmented digital images, wherein pores, grains, and organic content are defined in the segmented digital images;
  d) determining a rock property for at least one of the rock samples taken from a defined location inside the well using the segmented digital images;
  f) measuring in situ fluid properties and in situ well properties in the well using the NMR logging tool at the multiple locations;
  g) estimating the rock property in the well at the defined location using the measured in situ well properties obtained in step f);
  h) comparing the estimated rock property for the defined location with the rock property determined for the defined location; and
  i) analysing and validating the at least one rock property determined using the NMR logging tool as compared to the at least one rock property determined for the rock samples for the corresponding at least one of the one or more locations of the well.

* * * * *

UNITED STATES PATENT AND TRADEMARK OFFICE
CERTIFICATE OF CORRECTION

PATENT NO.           : 10,436,865 B2
APPLICATION NO.      : 15/543576
DATED                : October 8, 2019
INVENTOR(S)          : Kathryn Elizabeth Washburn Page 1 of 1

It is certified that error appears in the above-identified patent and that said Letters Patent is hereby corrected as shown below:

In the Claims

Column 22, Lines 3 through 5 in Claim No. 14 (iv), "Comparing the determined rock property with the estimated rock properly for a corresponding" should read -- COMPARING THE DETERMINED ROCK PROPERTY WITH THE ESTIMATED ROCK PROPERTY FOR A CORRESPONDING --.

Signed and Sealed this
Twenty-sixth Day of November, 2019

Andrei Iancu
*Director of the United States Patent and Trademark Office*